United States Patent [19]
Böttcher et al.

[11] Patent Number: 6,130,360
[45] Date of Patent: Oct. 10, 2000

[54] HYDROGENATION OF ALKINOLS USING A CATALYST CONTAINING MACROPORES

[75] Inventors: Arnd Böttcher, Frankenthal; Melanie Brunner, Schifferstadt; Jochem Henkelmann, Mannheim; Heinz Rütter, Hochdorf-Assenheim, all of Germany

[73] Assignee: BASF Aktiengesellschaft, Ludwigshafen, Germany

[21] Appl. No.: 09/207,622

[22] Filed: Dec. 9, 1998

[30] Foreign Application Priority Data

Dec. 12, 1997 [DE] Germany .................. 197 55 347

[51] Int. Cl.⁷ .................................................. C07C 27/00
[52] U.S. Cl. ........................................... 568/861; 568/903
[58] Field of Search ........................ 568/861, 903

[56] References Cited

U.S. PATENT DOCUMENTS

| | | | |
|---|---|---|---|
| 2,671,112 | 3/1954 | Inhoffen | 260/598 |
| 2,992,278 | 7/1961 | Tedeschi | 260/617 |
| 3,449,445 | 6/1969 | Wetherill | 260/635 |
| 3,759,845 | 9/1973 | Rudoff | 252/466 |
| 3,950,441 | 4/1976 | Rudoff et al. | 260/635 |
| 4,287,099 | 9/1981 | Baer et al. | 252/465 |
| 4,384,147 | 5/1983 | Baer et al. | 568/861 |
| 4,864,066 | 9/1989 | Mueller et al. | 568/861 |
| 5,068,468 | 11/1991 | Schossig et al. | 568/861 |
| 5,444,170 | 8/1995 | Vedage | 568/861 |

FOREIGN PATENT DOCUMENTS

| | | |
|---|---|---|
| 482445 | 4/1992 | European Pat. Off. . |
| 2145297 | 3/1972 | Germany . |
| 2023020 | 12/1979 | United Kingdom . |

*Primary Examiner*—Michael L. Shippen
*Attorney, Agent, or Firm*—Keil & Weinkauf

[57] ABSTRACT

An alkinol or mixture of two or more thereof is hydrogenated by bringing the alkinol or the mixture of two or more thereof into contact with a hydrogen-containing gas in the presence of a catalyst comprising as active metal at least one metal of transition group VIII of the Periodic Table, either alone or together with at least one metal of transition group I or VII of the Periodic Table, applied to a support, wherein the support contains macropores.

8 Claims, No Drawings

HYDROGENATION OF ALKINOLS USING A CATALYST CONTAINING MACROPORES

The present invention relates to a process for hydrogenating alkinols by bringing one or more alkinols into contact with a hydrogen-containing gas in the presence of a catalyst containing macropores.

Hydrogenations using a wide variety of catalysts are known from the prior art.

Thus, DE 195 00 479 describes the hydrogenation of acetylenic alcohols over Pd/C and Pt/C catalysts.

In DE-A 37 17 405, a catalyst based on a nickel salt is used for hydrogenating alkinols.

In U.S. Pat. No. 2,992,278, alkinols are hydrogenated in the presence of Pd, Rh or Pt in the presence of a small amount of base (e.g. KOH) to give the corresponding alkanediols.

DE-A 858 095 and DE-A 2 997 018 concern the hydrogenation of 1,4-butynediol in the presence of a catalyst comprising nickel, copper and manganese on silica extrudates. The process described there is carried out in one stage. The reaction temperatures are from 80 to 160° C. at a pressure of 300 bar.

Raney catalysts (copper, nickel) have also been described for such hydrogenations, e.g. in U.S. Pat. No. 3,449,445. According to this document, hydrogenation is carried out in a two-stage process first at 20 bar over the suspended Raney catalyst and then, in a second stage, at 120–140° C. over a fixed-bed catalyst.

GB-A 20 23 020 relates to catalysts for the hydrogenation of butynediol, which catalysts comprise both Pd and Ru as active components.

Although, as can be seen from the above summary of the prior art, numerous catalysts have already been used for the hydrogenation of alkinols, the selectivity achieved and the space-time yields in which the corresponding alkanols or alkanediols were obtained remained below what would have been desirable to meet the ever greater expectations in respect of product purity or to carry out the corresponding processes in a really economical manner.

It is an object of the present invention to provide a process for hydrogenating alkinols, by means of which the corresponding alkanols or alkanediols can be obtained in very high selectivity and space-time yield without significant secondary reactions.

The present invention accordingly provides a process for hydrogenating an alkinol or a mixture of two or more thereof by bringing the alkinol or the mixture of two or more thereof into contact with a hydrogen-containing gas in the presence of a catalyst comprising as active metal at least one metal of transition group VIII of the Periodic Table, either alone or together with at least one metal of transition group I or VII of the Periodic Table, applied to a support, wherein the support contains macropores.

In a preferred embodiment, the present invention provides a process for hydrogenating an alkinol or a mixture of two or more thereof, as defined above, where the catalyst (catalyst 1) comprises as active metal at least one metal of transition group VIII of the Periodic Table, either alone or together with at least one metal of transition group I or VII of the Periodic Table, applied to a support, wherein the support has a mean pore diameter of at least 50 nm and a BET surface area of not more than 30 m$^2$/g and the amount of active metal is from 0.01 to 30% by weight, based on the total weight of the catalyst.

The present invention further provides, in a preferred embodiment, a process as defined above, in which the catalyst (catalyst 2) comprises as active metal at least one metal of transition group VIII of the Periodic Table, either alone or together with at least one metal of transition group I or VII of the Periodic Table, in an amount of from 0.01 to 30% by weight, based on the total weight of the catalyst, applied to a support, wherein from 10 to 50% of the pore volume of the support is made up by macropores having a pore diameter in the range from 50 nm to 10,000 nm and from 50 to 90% of the pore volume of the support is made up by mesopores having a pore diameter in the range from 2 to 50 nm, where the sum of the pore volumes adds up to 100%.

In a further, preferred embodiment, the present invention provides a process, as defined above, in which the catalyst (catalyst 3) comprises as active metal at least one metal of transition group VIII of the Periodic Table, either alone or together with at least one metal of transition group I or VII of the Periodic Table, in an amount of from 0.01 to 30% by weight, based on the total weight of the catalyst, applied to a support, wherein the support has a mean pore diameter of at least 0.1 µm and a BET surface area of not more than 15 m$^2$/g.

The active metals used can in principle be any metals of transition group VIII of the Periodic Table. The active metals used are preferably platinum, rhodium, palladium, cobalt, nickel or ruthenium or a mixture of two or more thereof, with particular preference being given to using ruthenium as active metal. Among the metals of transition group I or VII or else I and VII of the Periodic Table, which are likewise all useable in principle, preference is given to using copper and/or rhenium.

The terms "macropores" and "mesopores" are used for the purposes of the present invention as they are defined in Pure Appl. Chem., 45, p. 79 (1976), namely as pores whose diameter is above 50 nm (macropores) or whose diameter is from 2 nm to 50 nm (mesopores).

The amount of active metal present is generally from about 0.01 to about 30% by weight, preferably from about 0.01 to about 5% by weight and in particular from about 0.1 to about 5% by weight, in each case based on the total weight of the catalyst used; the contents preferably used in the preferred catalysts 1 to 3 described below will again be indicated individually in the discussion of these catalysts.

The term "alkinol" encompasses in principle all compounds which contain both at least one C—C triple bond and one or more hydroxyl groups. Preference is given to reacting alkynemonools, i.e. compounds containing a C—C triple bond and one hydroxyl group, or else alkynediols, i.e. compounds containing a C—C triple bond and two hydroxyl groups. The compounds which are preferably used are again explained briefly below in the section "Carrying out the process".

The preferred catalysts 1 to 3 will now be described in detail below. The descriptions will be based, by way of example, on the use of ruthenium as active metal. The information below can also be applied analogously to the other active metals which can be used.

Catalyst 1

The catalysts 1 used according to the present invention can be produced industrially by applying at least one metal of transition group VIII of the Periodic Table and, if desired, at least one metal of transition group I or VII of the Periodic Table to a suitable support.

The application can be achieved by steeping the support in aqueous metal salt solutions, e.g. aqueous ruthenium salt solutions, by spraying such metal salt solutions onto the support or by other suitable methods. Suitable metal salts of transition group I, VII or VIII of the Periodic Table are the nitrates, nitrosyl nitrates, halides, carbonates, carboxylates, acetylacetonates, chloro complexes, nitrito complexes or amine complexes of the corresponding metals, with preference being given to the nitrates and nitrosyl nitrates.

In the case of catalysts which comprise not only the metal of transition group VIII of the Periodic Table but also further metals as active metal applied to the support, the metal salts or metal salt solutions can be applied simultaneously or in succession.

The supports coated or impregnated with the metal salt solution are subsequently dried, preferably at from 100° C. to 150° C., and, if desired calcined at from 200° C. to 600° C., preferably from 350° C. to 450° C. If separate solutions are applied, the catalyst is dried and if desired calcined, as described above, after each impregnation step. The order in which the active components are applied is immaterial.

Subsequently, the coated and dried and, if desired, calcined supports are activated by treatment in a gas stream comprising free hydrogen at from about 30° C. to about 600° C., preferably from 150° C. to about 450° C. The gas stream preferably consists of from 50 to 100% by volume of $H_2$ and from 0 to 50% by volume of $N_2$.

The metal salt solution or solutions is/are applied to the support or supports in such an amount that the total content of active metal, in each case based on the total weight of the catalyst, is from about 0.01 to about 30% by weight, preferably from about 0.01 to about 5% by weight, more preferably from about 0.01 to about 1% by weight and in particular from about 0.05 to about 1% by weight.

The total surface area of the metal on the catalyst 1 is preferably from about 0.01 to about 10 $m^2/g$, more preferably from about 0.05 to about 5 $m^2/g$ and in particular from about 0.05 to about 3 $m^2/g$ of the catalyst. The metal surface area is determined by means of the chemisorption method of J. LeMaitre et al., in "Characterization of Heterogenous Catalysts", edited by Francis Delanney, Marcel Dekker, New York 1984, pp. 310–324.

In catalyst 1 used according to the present invention, the ratio of the surface areas of the active metal/metals and the catalyst support is preferably less than about 0.05, with the lower limit being about 0.0005.

The support materials which can be used for producing the catalysts used according to the present invention are those which are macroporous and have a mean pore diameter of at least about 50 nm, preferably at least about 100 nm, in particular at least about 500 nm, and whose BET surface area is not more than about 30 $m^2/g$, preferably not more than about 15 $m^2/g$, more preferably not more than about 10 $m^2/g$, in particular not more than about 5 $m^2/g$ and more preferably not more than about 3 $m^2/g$. Expressed more precisely, the mean pore diameter of the support is preferably from about 100 nm to about 200 $\mu$m, more preferably from about 500 nm to about 50 $\mu$m. The surface area of the support is preferably from about 0.2 to about 15 $m^2/g$, more preferably from about 0.5 to about 10 $m^2/g$, in particular from about 0.5 to about 5 $m^2/g$ and most preferably from about 0.5 to about 3 $m^2/g$.

The surface area of the support is determined by the BET method using $N_2$ adsorption, in particular in accordance with DIN 66131. The mean pore diameter and the pore size distribution are determined by Hg porosimetry, in particular in accordance with DIN 66133.

The pore size distribution of the support is preferably approximately bimodal; the pore diameter distribution having maxima at about 600 nm and about 20 $\mu$m in the bimodal distribution represents a specific embodiment of the invention.

Further preference is given to a support having a surface area of 1.75 $m^2/g$ and this bimodal distribution of the pore diameter. The pore volume of this preferred support is preferably about 0.53 ml/g.

Macroporous support materials which can be used are, for example, activated carbon, silicon carbide, aluminum oxide, silicon dioxide, titanium dioxide, zirconium dioxide, magnesium oxide, zinc oxide or mixtures of two or more thereof, with preference being given to using aluminum oxide and zirconium dioxide.

Further details regarding catalyst 1 or its production may be found in DE-A 196 24 484.6, whose relevant contents are fully incorporated by reference into the present application.

Catalyst 2

The catalysts 2 used according to the present invention can be produced industrially by applying an active metal of transition group VIII of the Periodic Table, preferably ruthenium or palladium and, if desired, at least one metal of transition group I or VII of the Periodic Table to a suitable support. The application can be achieved by steeping the support in aqueous metal salt solutions, e.g. ruthenium or palladium salt solutions, by spraying such metal salt solutions onto the support or by other suitable methods. Suitable metal salts for preparing the metal salt solutions are the nitrates, nitrosyl nitrates, halides, carbonates, carboxylates, acetylacetonates, chloro complexes, nitrito complexes or amine complexes of the corresponding metals, with preference being given to the nitrates and nitrosyl nitrates.

In the case of catalysts which comprise a plurality of active metals applied to the support, the metal salts or metal salt solutions can be applied simultaneously or in succession.

The supports coated or impregnated with the metal salt solution are subsequently dried, preferably at from 100° C. to 150° C. If desired, these supports can be calcined at from 200° C. to 600° C., preferably from 350° C. to 450° C. The coated supports are subsequently activated by treatment in a gas stream comprising free hydrogen at from 30° C. to 600° C., preferably from 100° C. to 450° C. and in particular from 100° C. to 300° C. The gas stream preferably consists of from 50 to 100% by volume of $H_2$ and from 0 to 50% by volume of $N_2$.

If a plurality of active metals are applied to the supports and if the application is carried out in succession, the support can be dried at from 100° C. to 150° C. and, if desired, calcined at from 200° C. to 600° C. after each application or impregnation. Here, the order in which the metal salt solutions are applied is immaterial.

The metal salt solution is applied to the support or supports in such an amount that the active metal content is from 0.01 to 30% by weight, preferably from 0.01 to 10% by weight, particularly preferably from 0.01 to 5% by weight and in particular from 0.3 to 1% by weight, based on the total weight of the catalyst.

The total surface area of the metal on the catalyst is preferably from 0.01 to 10 $m^2/g$, particularly preferably from 0.05 to 5 $m^2/g$ and more preferably from 0.05 to 3 $m^2/g$ of the catalyst. The metal surface area is measured by the chemisorption method, as described in J. LeMaitre et al., "Characterization of Heterogeneous Catalysts", edited by Francis Delanney, Marcel Dekker, New York (1984), pp. 310–324.

In catalyst 2 used according to the present invention, the ratio of the surface areas of the active metal or metals and the catalyst support is less than about 0.3, preferably less than about 0.1 and in particular about 0.05 or less, with the lower limit being about 0.0005.

The support materials which can be used for producing catalysts 2 used according to the present invention contain macropores and mesopores.

Here, the supports which can be used according to the invention have a pore distribution in which from about 5 to about 50%, preferably from about 10 to about 45%, more preferably from about 10 to about 30% and in particular from about 15 to about 25% of the pore volume is made up by macropores having a pore diameter in the range from about 50 nm to about 10,000 nm and from about 50 to about 95%, preferably from about 55 to about 90%, more preferably from about 70 to about 90% and in particular from about 75 to about 85% of the pore volume is made up by mesopores having a pore diameter of from about 2 to about 50 nm, where in each case the sum of the pore volumes adds up to 100%.

The total pore volume of the supports used according to the present invention is from about 0.05 to 1.5 cm$^3$/g, preferably from 0.1 to 1.2 cm$^3$/g and in particular from 0.3 to 1.0 cm$^3$/g. The mean pore diameter of the supports used according to the present invention is from about 5 to 20 nm, preferably from about 8 to 15 nm and in particular from about 9 to about 12 nm.

The surface area of the support is preferably from about 50 to about 50 m$^2$/g, more preferably from about 200 to about 350 m$^2$/g and in particular from about 200 to about 250 m$^2$/g of the support.

The surface area of the support is determined by the BET method using N$_2$ adsorption, in particular in accordance with DIN 66131. The mean pore diameter and the size distribution are determined by Hg porosimetry, in particular in accordance with DIN 66133.

Although, in principle, production of the catalyst can be carried out using all known support materials which have the above-defined pore size distribution, preference is given to using activated carbon, silicon carbide, aluminum oxide, silicon dioxide, titanium dioxide, zirconium dioxide, magnesium oxide, zinc oxide or mixtures thereof, more preferably aluminum oxide and zirconium dioxide.

Further details regarding catalyst 2 or its production may be found in DE-A 196 24 485.4, the relevant contents of which are fully incorporated by reference into the present application.

Catalyst 3

The catalysts 3 used according to the present invention can be produced industrially by applying an active metal of transition group VIII of the Periodic Table and, if desired, at least one metal of transition group I or VII of the Periodic Table to a suitable support. The application can be achieved by steeping the support in aqueous metal salt solutions such as ruthenium salt solutions, by spraying such metal salt solutions onto the support or by other suitable methods. Salts which are suitable as ruthenium salts for preparing the ruthenium salt solutions and also as metal salts of transition group I, VII or VIII are the nitrates, nitrosyl nitrates, halides, carbonates, carboxylates, acetylacetonates, chloro complexes, nitrito complexes or amine complexes of the corresponding metals, with preference being given to the nitrates and nitrosyl nitrates.

In the case of catalysts which comprise a plurality of metals applied to the support, the metal salts or metal salt solutions can be applied simultaneously or in succession.

The supports coated or impregnated with the ruthenium salt solution or metal salt solution are then dried, preferably at from 100° C., to 150° C. and, if desired, calcined at from 200° C. to 600° C.

The coated supports are subsequently activated by treating the coated supports in a gas stream comprising free hydrogen at from 30 to 600° C., preferably from 150 to 450° C. The gas stream preferably consists of from 50 to 100% by volume of H$_2$ and from 0 to 50% by volume of N$_2$.

If metals of transition group I or VII are applied to the supports in addition to the active metal of transition group VIII of the Periodic Table and the application is carried out in succession, the support can be dried at from 100° C. to 150° C. and, if desired, calcined at from 200 to 600° C. after each application or impregnation. Here, the order in which the metal salt solutions are applied is immaterial.

The metal salt solution is applied to the support or supports in such an amount that from 0.01 to 30% by weight, based on the total weight of the catalyst, of active metal are present on the support. This amount is preferably from 0.2 to 15% by weight, particularly preferably about 0.5% by weight.

The total surface area of the metal on the catalyst 3 is preferably from 0.01 to 10 m$^2$/g, particularly preferably from 0.05 to 5 m$^2$/g, in particular from 0.05 to 3 m$^2$ per g of the catalyst.

The support materials which can be used for producing the catalysts 3 used according to the present invention are preferably those which are macroporous and have a mean pore diameter of at least 0.1 μm, preferably at least 0.5 μm, and a surface area of not more than 15 m$^2$/g, preferably not more than 10 m$^2$/g, particularly preferably not more than 5 m$^2$/g, in particular not more than 3 m$^2$/g. The mean pore diameter of the support is preferably in a range from 0.1 to 200 μm, in particular from 0.5 to 50 μm. The surface area of the support is preferably from 0.2 to 15 m$^2$/g, particularly preferably from 0.5 to 10 m$^2$/g, in particular from 0.5 to 5 m$^2$/g, especially from 0.5 to 3 m$^2$ per g of the support.

The surface area of the support is determined by the BET method using N$_2$ adsorption, in particular in accordance with DIN 66131. The mean pore diameter and the pore size distribution are determined by Hg porosimetry, in particular in accordance with DIN 66133. The pore size distribution of the support is preferably approximately bimodal; the pore diameter distribution having maxima at about 0.6 μm and about 20 μm in the bimodal distribution represents a specific embodiment of the invention.

Particular preference is given to a support having a surface area of about 1.75 m$^2$/g and having this bimodal distribution of the pore diameter. The pore volume of this preferred support is preferably about 0.53 ml/g.

Macroporous support materials which can be used are, for example, activated carbon, silicon carbide, aluminum oxide, silicon dioxide, titanium dioxide, zirconium dioxide, magnesium oxide, zinc oxide or mixtures thereof. Preference is given to aluminum oxide and zirconium dioxide.

Further details regarding catalyst 3 and its production may be found in DE-A 196 04 791.9, whose relevant contents are fully incorporated by reference into the present application.

Carrying out the process

In the process of the present invention, the hydrogenation is generally carried out at from about 50 to 250° C., preferably from about 70 to 220° C. The pressures employed are generally above 10 bar, preferably from about 20 to about 300 bar.

The process of the present invention can be carried out either continuously or batchwise, preference being given to carrying out the process continuously.

In the continuous procedure, the amount of alkinol to be hydrogenated or of the mixture of two or more thereof is preferably from about 0.05 to about 3 kg per liter of catalyst per hour, more preferably from about 0.1 to about 1 kg per liter of catalyst per hour.

Hydrogenation gases which can be used are any gases which comprise free hydrogen and do not contain any harmful amounts of catalyst poisons such as CO. For example, it is possible to use tailgases from reformers. Preference is given to using pure hydrogen as hydrogenation gas.

the hydrogenation according to the present invention can be carried out in the absence or presence of a solvent or diluent, i.e. it is not necessary to carry out the hydrogenation in solution.

However, preference is given to using a solvent or diluent, in which case any suitable solvent or diluent can be used. The choice is not critical as long as the solvent or diluent used is able to form a homogeneous solution with the alkinol to be hydrogenated. For example, the solvents or diluents can also comprise water.

Examples of suitable solvents or diluents include the following:

straight-chain or cyclic ethers such as tetrahydrofuran or dioxane, and also aliphatic alcohols in which the alkyl radical preferably has from 1 to 10 carbon atoms, in particular from 3 to 6 carbon atoms.

Examples of preferred alcohols are i-propanol, n-butanol, i-butanol and n-hexanol.

Mixtures of these or other solvents or diluents can likewise be used.

The amount of solvent or diluent used is not restricted in any particular way and can be freely chosen as required, however, preference is given to amounts which lead to a 10–70% strength by weight solution of the alkinol to be hydrogenated.

In the process of the present invention, particular preference is given to using the product formed in the hydrogenation, i.e. the alkanol, as solvent, if desired together with other solvents or diluents. In any case, part of the product formed in the process can be mixed into the alkinol to be hydrogenated. Preference is given to mixing in the reaction product as solvent as diluent in an amount corresponding to from 1 to 30 times, particularly preferably from 5 to 20 times, in particular from 5 to 10 times, the weight of the compound to be hydrogenated.

As already indicated above, the term "akinol" used for the purposes of the present invention encompasses both alkynemonools and also alkynediols or alkynepolyols, with preference being given to reacting alkynediols.

Examples which may be mentioned are, in particular:
propargyl alcohol, 2,3-butyn-1-ol, 1,4-butynediol, 1,6-hexynediol, 2,5-dimethylhexynediol, 1,8-octynediol, dehydrolinalool or a mixture of two or more thereof.

The process of the present invention is illustrated below with the aid of a few examples.

EXAMPLES

Example of Catalyst Production

A mesoporous/macroporous aluminum oxide support in the form of 4 mm extrudates which had a BET surface area of 238 $m^2/g$ and a pore volume of 0.45 ml/g was impregnated with an aqueous ruthenium(I) nitrate solution having a concentration of 0.8% by weight. 0.15 ml/g (about 33% of the total volume) of the pores of the support had a diameter in the range from 50 nm to 10,000 nm and 0.30 ml/g (about 67% of the total pore volume) of the pores of the support had a pore diameter in the range from 2 to 50 nm. The solution volume taken up by the support during impregnation corresponded approximately to the pore volume of the support used.

Subsequently, the support impregnated with the ruthenium(III) nitrate solution was dried at 120° C. and activated (reduced) at 200° C. in a stream of hydrogen. The catalyst produced in this way contained 0.05% by weight of ruthenium, based on the weight of the catalyst.

Example 1

In a 300 ml pressure reactor, 10 g of the supported Ru catalyst were placed in a catalyst basket insert and 160 g (0.33 mol) of a 30% strength solution of 2,5-dimethylhexynediol in isopropanol were added. The hydrogenation was carried out using pure hydrogen at a constant pressure of 30 bar and a temperature of 140° C. Hydrogenation was continued until no more hydrogen was absorbed (2.5 hours). The reactor was subsequently vented. The alkyne conversion was 100% and the yield of 2,5-dimethylhexanediol was 97%, based on the amount of 2,5-dimethyl-hexynediol used.

Example 2

An upright stainless steel reaction tube having an internal diameter of 30 mm and a length of 1.7 m was charged with 800 ml of the Ru catalyst described in the catalyst production example. In the upflow mode, 0.8 kg/h of a 30% strength solution of 2,5-dimethylhexynediol in isobutanol together with pure hydrogen were pumped through the upright reaction tube from the bottom upward at a mean temperature of 130° C. and a pressure of 30 bar. Part of the reaction product was, after leaving the upright reaction tube, pumped back into the reactor together with fresh 2,5-dimethylhexynediol solution. The remaining reaction product was depressurized in a receiver. Using analysis of the tailgas for monitoring, hydrogenation was carried out using a 10% excess of hydrogen over the theoretically required amount. Gas-chromatographic analysis of the reaction product shows that 100% of the alkyne had been converted. 2,5-Dimethylhexanediol was able to be obtained at a selectivity of 97%, based on the amount of 2,5-dimethylhexynediol used. The catalyst operating life under the conditions selected was at least 2200 hours without a decrease in activity and selectivity being observed.

Example 3

In a 300 ml pressure reactor, 10 g of the Ru catalyst as described in the catalyst production example were placed in a catalyst basket insert and 150 g (0.87 mol) of a 50% strength aqueous butynediol solution were added. The hydrogenation was carried out using pure hydrogen at a constant pressure of 40 bar and a temperature of 80° C. Hydrogenation was continued until no more hydrogen was absorbed (3 hours). The reactor was subsequently vented. The conversion of the alkyne was 100% and the yield of 1,4-butanediol was 92%, based on the amount of butynediol used.

Example 4

In a 300 ml pressure reactor, 10 g of the Ru catalyst as described in the catalyst production example were placed in a catalyst basket insert and 150 g (0.99 mol) of dehydrolinalool were added. The hydrogenation was carried out using pure hydrogen at a constant pressure of 40 bar and a temperature of 80° C. After a reaction time of 4 hours, the reactor was vented. The conversion of dehydrolinalool was 95% and linalool was obtained in a selectivity of 90%.

As the examples show, the process of the present invention makes it possible to convert alkinols into the corresponding alkanols or alkanediols at high selectivity and high space-time yield. Furthermore, no significant secondary reactions are observed. In addition, the catalysts used have an extremely long operating life. A further advantage of the process of the present invention is that the hydrogenation can also be carried out at relatively low pressures of, for example, from 20 to 50 bar, so that, overall, comparatively low capital costs for the pressure vessels used are incurred.

We claim:

1. A process for hydrogenating an alkinol or a mixture of two or more thereof by bringing the alkinol or the mixture of two or more thereof into contact with a hydrogen-containing gas in the presence of a catalyst comprising ruthenium as active metal, either alone or together with at least one metal of transition group I or VII of the Periodic Table, applied to a support, wherein the support contains macropores.

2. A process as claimed in claim 1, wherein the catalyst comprises as active metal at least one metal of transition group VIII of the Periodic Table, either alone or together with at least one metal of transition group I or VII of the Periodic Table, applied to a support, wherein the support has a mean pore diameter of at least 50 nm and a BET surface area of not more than 30 $m^2/g$ and the amount of active metal is from 0.01 to 30% by weight, based on the total weight of the catalyst.

3. A process as claimed in claim 1, wherein the catalyst comprises as active metal at least one metal of transition group VII of the Periodic Table, either alone or together with at least one metal of transition group I or VII of the Periodic Table, in an amount of from 0.01 to 30% by weight, based on the total weight of the catalyst, applied to a support, wherein from 10 to 50% of the pore volume of the support is made up by macropores having a pore diameter in the range from 50 nm to 10,000 nm and from 50 to 90% of the pore volume of the support is made up by mesopores having a pore diameter in the range from 2 to 50 nm, where the sum of the pore volumes adds up to 100%.

4. A process as claimed in claim 1, wherein the catalyst comprises as active metal at least one metal of transition group VIII of the Periodic Table, either alone or together with at least one metal of transition group I or VII of the Periodic Table, in an amount of from 0.01 to 30% by weight, based on the total weight of the catalyst, applied to a support, wherein the support has a mean pore diameter of at least 0.1 $\mu$m and a BET surface area of not more than 15 $m^2/g$.

5. A process as claimed in claim 1, wherein the alkinol is selected from the group consisting of propargyl alcohol, 2,3-butyn-1-ol, 1,4-butynediol, 1,6-hexynediol, 2,5-dimethyl-hexynediol, 1,8-octynediol, dehydrolinalool and mixtures of two or more thereof.

6. A process as claimed in claim 1, wherein the support comprises activated carbon, silicon carbide, aluminum oxide, silicon dioxide, titanium dioxide, zirconium dioxide, magnesium oxide, zinc oxide or a mixture of two or more thereof.

7. A process as claimed in claim 1, wherein the hydrogenation is carried out in the presence of a solvent or diluent.

8. A process as claimed in claim 1, wherein the hydrogenation is carried out continuously.

* * * * *